(12) United States Patent
Dillon et al.

(10) Patent No.: US 6,235,006 B1
(45) Date of Patent: May 22, 2001

(54) NEEDLE GUARD AND ASSEMBLY

(75) Inventors: Jagmohanbir Singh Dillon; William Leonard Mobbs, both of Canberra (AU)

(73) Assignee: Noble House Group Pty. Ltd., Fishwyck (AU)

( * ) Notice: Subject to any disclaimer, the term of this patent is extended or adjusted under 35 U.S.C. 154(b) by 0 days.

(21) Appl. No.: 09/486,041

(22) PCT Filed: Sep. 11, 1998

(86) PCT No.: PCT/AU98/00752

§ 371 Date: Feb. 18, 2000

§ 102(e) Date: Feb. 18, 2000

(87) PCT Pub. No.: WO99/12594

PCT Pub. Date: Mar. 18, 1999

(30) Foreign Application Priority Data

Sep. 11, 1997 (AU) .................................................. PO 9157

(51) Int. Cl.[7] .................................................... A61M 5/00
(52) U.S. Cl. ........................ 604/263; 604/192; 604/162; 604/171
(58) Field of Search .................................. 604/263, 110, 604/187, 192, 198, 162, 171

(56) References Cited

U.S. PATENT DOCUMENTS

| | | |
|---|---|---|
| 4,676,783 | 6/1987 | Jagger et al. . |
| 4,929,241 | 5/1990 | Kulli . |
| 4,941,881 | 7/1990 | Masters et al. . |
| 5,069,341 | 12/1991 | Barbieri et al. . |
| 5,088,982 | 2/1992 | Ryan . |
| 5,112,311 | 5/1992 | Utterberg et al. . |
| 5,120,320 | 6/1992 | Fayngold . |
| 5,167,640 | 12/1992 | Balding . |
| 5,192,275 | 3/1993 | Burns . |
| 5,279,588 | 1/1994 | Nicoletti et al. . |
| 5,290,264 | 3/1994 | Utterberg . |
| 5,330,438 | 7/1994 | Gollobin et al. . |
| 5,350,368 | 9/1994 | Shields . |
| 5,382,240 | 1/1995 | Lam . |
| 5,401,250 | 3/1995 | Shields . |
| 5,433,703 | 7/1995 | Utterberg et al. . |
| 5,498,241 | 3/1996 | Fabozzi . |
| 5,562,636 | 10/1996 | Utterberg . |
| 5,562,637 | 10/1996 | Utterberg . |
| 5,827,239 | 10/1998 | Dillon et al. . |

FOREIGN PATENT DOCUMENTS

| | | |
|---|---|---|
| 0 722 749 A1 | 7/1996 | (EP) . |
| WO 94/05205 | 3/1994 | (WO) . |

*Primary Examiner*—John D. Yasko
(74) *Attorney, Agent, or Firm*—Shanks & Herbert

(57) ABSTRACT

Needle guards are disclosed for use with needle assemblies comprising a needle hub that joins a flexible trailing tube to a medical needle, the normally open front ends of the guards being closeable after a needle and hub have been pulled therein by the trailing tube. In one example (FIG. 4c), a guard (10) has a stiff upper sidewall (24a) of an inverted U-shape and a flexible lower sidewall (26b) that fits inside the upper sidewall and is resiliently biased to bring its front end (31) into contact with the front end (30) of upper sidewall (24b) so as to close the front aperture of the guard after the needle assembly (16) has been withdrawn into the guard. The lower sidewall (26b) can be locked or clipped into the upper sidewall (24b) by pressing lower sidewall passed catches (72). In this way, the needle is completely and safely enclosed after use to reduce the danger of needle-stick injury and blood-splash contamination.

12 Claims, 4 Drawing Sheets

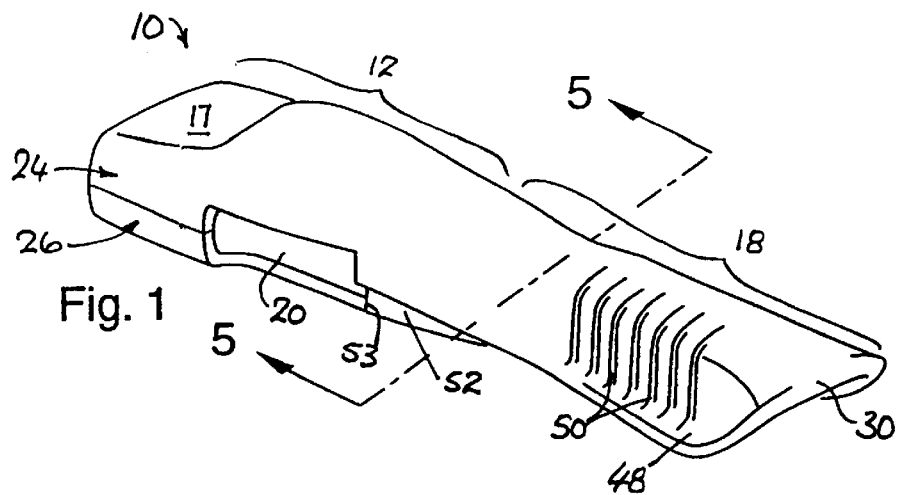
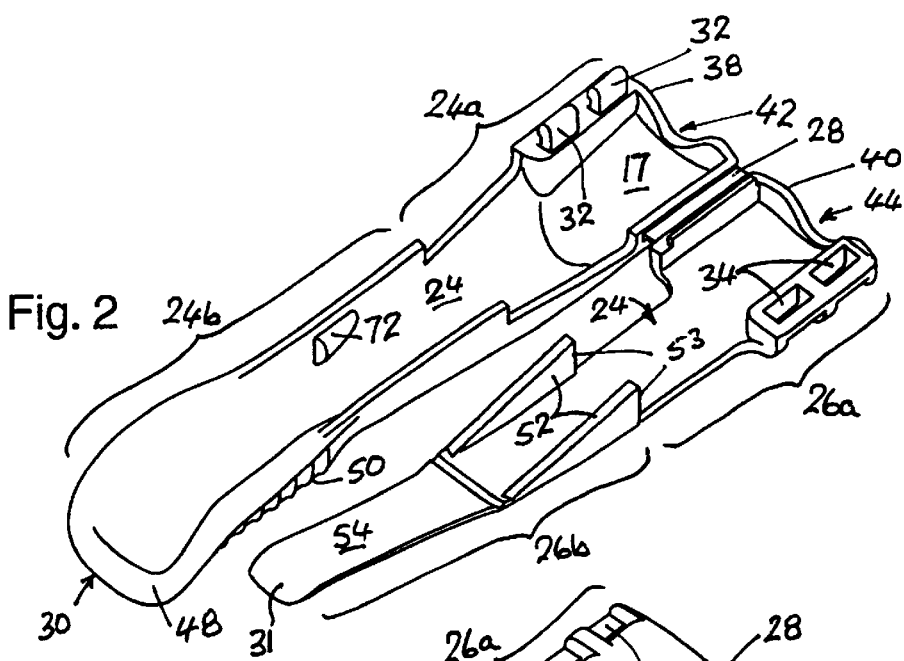
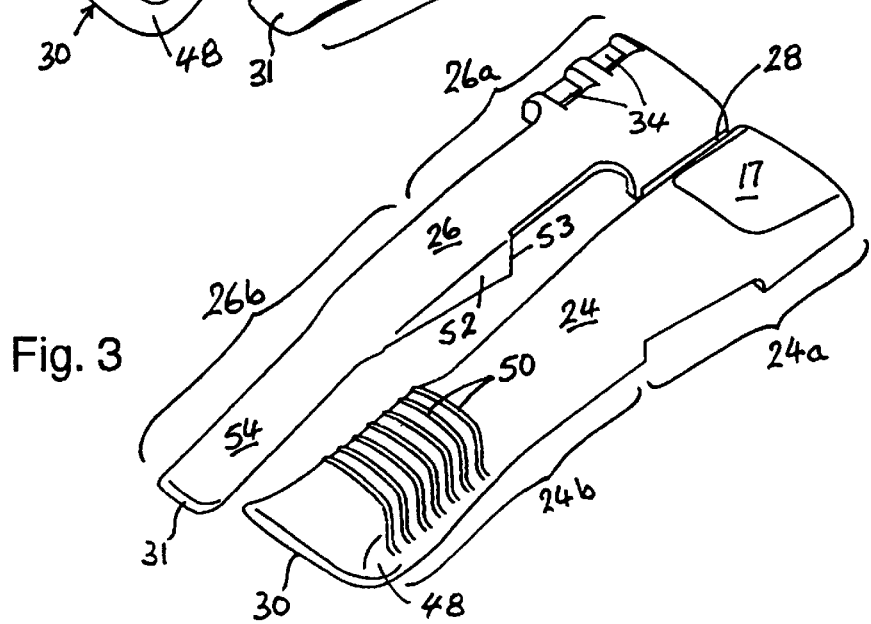

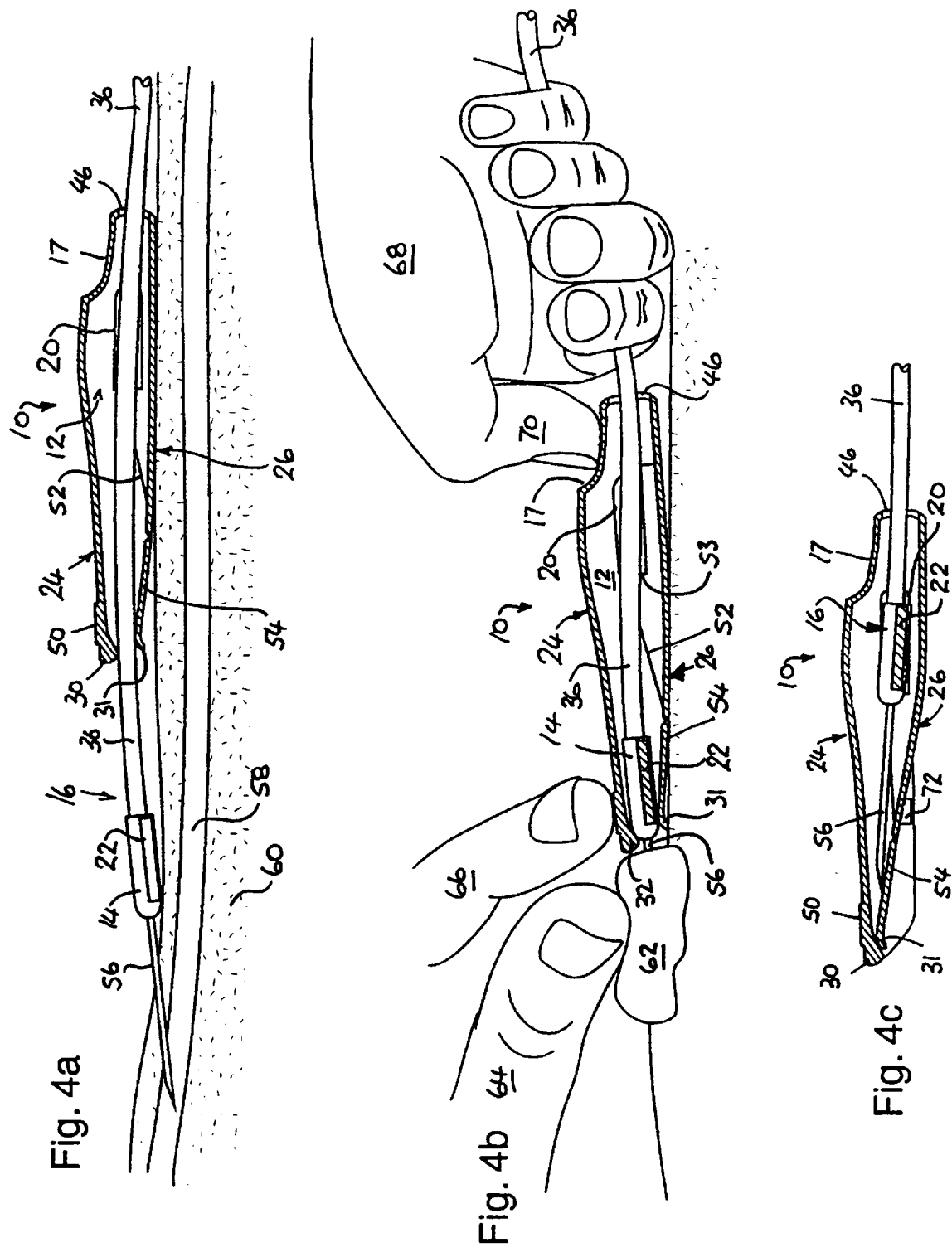

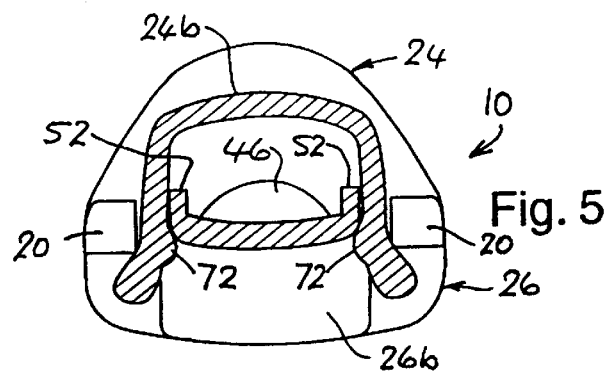
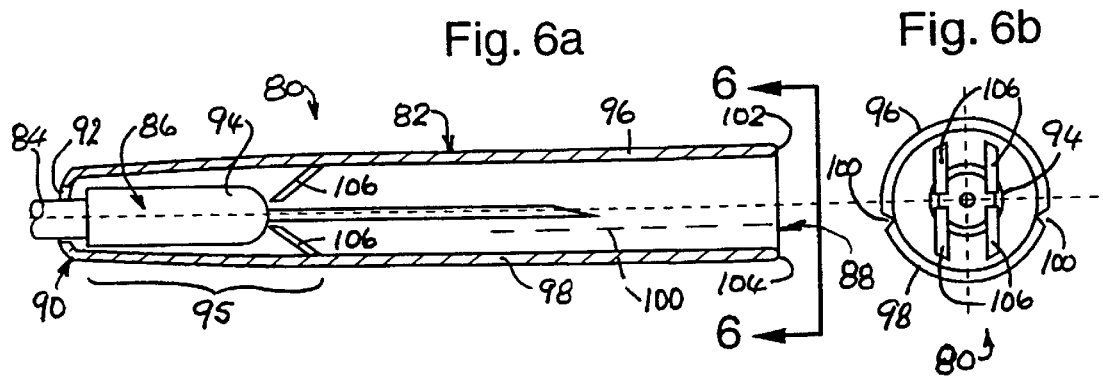
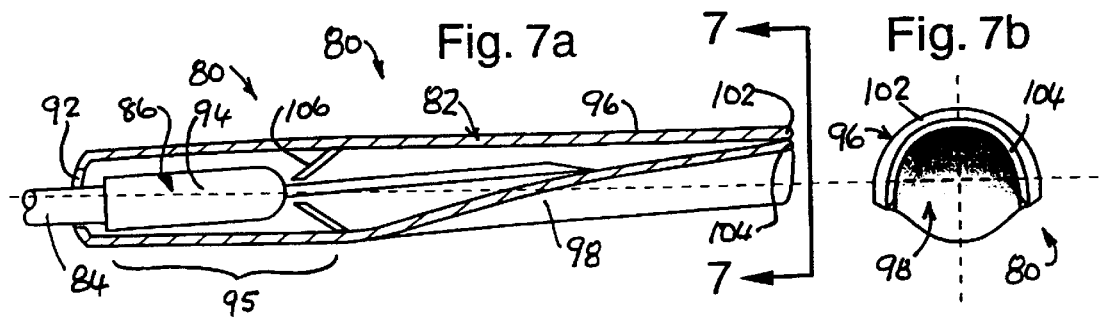
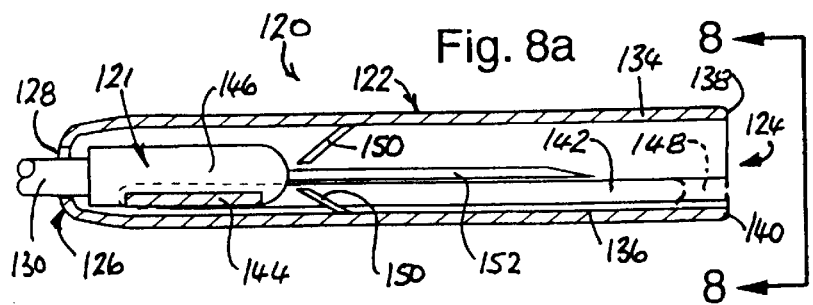

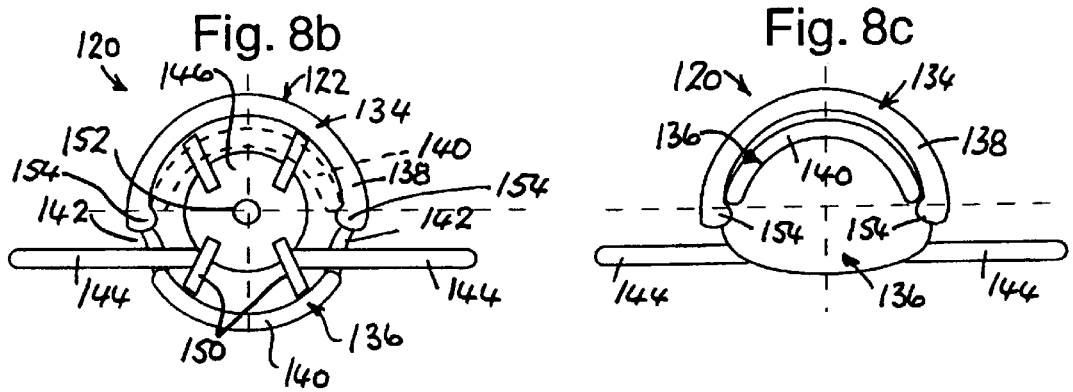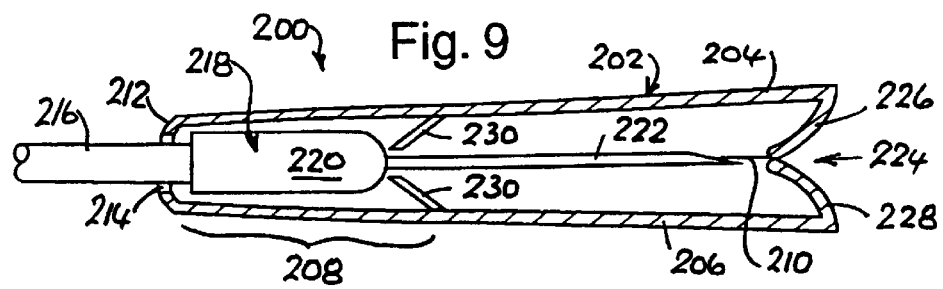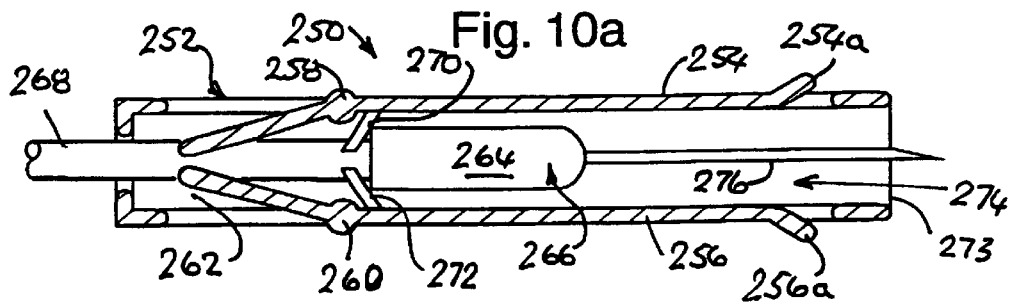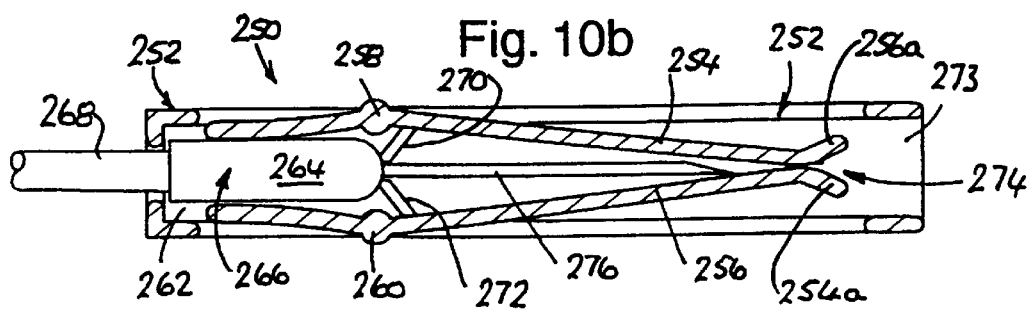

NEEDLE GUARD AND ASSEMBLY

TECHNICAL FIELD

This invention relates to guards for use with needle assemblies and to combined guard and needle assemblies.

The needle assemblies concerned are those which have a tubular medical needle pointed at the front end and joined by a hub at the rear or butt end to a flexible trailing tube so that fluids can be conveyed to or from a patient via the tube and needle. The hub is commonly formed from plastic, injection-moulded onto the needle and used to hold the needle during insertion. One or two flexible lateral wing-like extensions may be moulded integrally with the hub to assist in manipulating the needle and in strapping the assembly to the patient, after the needle has been inserted into a vein. Such needles are called 'butterfly' or 'winged' needles and are typically used for intravenous infusion or phlebotomy. Needle assemblies without wings formed on their hubs are called 'wingless' and are commonly used in blood collection. The guards of the present invention are applicable to both wingless and winged needle assemblies.

BACKGROUND TO THE INVENTION

The desirability of guarding medical needles to reduce needle-stick injury is well recognised, as is the desirability of reducing blood-splash from needles immediately after use. 'Blood-splash' is used herein generically to signify the dripping of any liquid from the point of a used needle and is a particular danger with needle assemblies because their trailing tubes often contain blood. There are other important desiderata of a more practical nature relating to needle guards: the guard should not interfere with the positioning and control of the needle during use; since many medical needles are manufactured without guards, the guard should be easy and safe to fit to a pre-existing needle assembly; on the other hand, it should be suitable for fitting to needle assemblies at the time of manufacture; and, since most needles will be used only once, the guard also needs to be inexpensive and disposable. The most pertinent prior art known to the applicant which addresses such desiderata is referenced below.

The guards of relevance to this invention are of two general classes: (i) those which fit around and slide along the trailing tube and over the needle from its rear end, and (ii) those which permanently house the needle in such a way that it can be extended from the guard for use or withdrawn into the guard for protection. Guards of the first class have the advantage that they can be moved well clear of the needle along the trailing tube so that the needle can be inserted without interference from the guard. Furthermore, guards of the first class can be easily attached around the trailing tube of a standard needle by the user, whereas those of the second are generally applied to the needle during manufacture and require the use of non-standard needle assemblies.

Guards of the first class may be divided into three types. First, there are those in which the front ends are split longitudinally into fingers that flex outwards when the guard is pushed onto the hub. The fingers typically ride along the needle wings and then snap together around the wings to retain the needle in a guarded position. Examples are disclosed in the applicant's US patent No. 5,827,239 which can be assembled by the user around the trailing tube of a standard winged needle assembly or fitted over the tube at the time of manufacture to form a combined needle and guard assembly. Others are disclosed in U.S. Pat. No. 5,069,341 to Barbieri et al, U.S. Pat. No. 5,192,275 to Burns, U.S. Pat. No. 5,330,438 to Gollobin, U.S. Pat. No. 5,279,588 to Nicoletti, U.S. Pat. No. 5,350,368 to Shields and U.S. Pat. Nos. 5,562,636 and 5,562,637 to Utterberg. Guards of this type are not ideal because blood splash can occur through their open front ends and/or side slots.

The prior art of the first type which is of most interest from the standpoint of the present invention is the embodiment illustrated in FIGS. 24 to 26 of the Nicoletti patent identified above, in which the front end of a tubular guard comprises two opposing fingers hingedly attached to the rear portion of the guard. Each finger has a hole therethrough to take one wing of the needle. To fit such a guard over a needle, the needle must be withdrawn from the patient and the fingers manipulated to fit the wings into the holes. Then the fingers must be pushed together to enclose the needle. Not only is there danger of needle stick blood-splash from the exposed used needle during this manoeuvre, but the user is likely to touch the sides of the exposed needle as he/she attempts to insert the wings into their slots in the fingers of the guard.

The second type of tube-mounted guard is also intend for use with winged needle assemblies but it has a single wide open-ended slot so that the needle can be withdrawn into the guard by folding its wings together and entering both wings into the slot. Examples of this type of guard are disclosed in U.S. Pat. No. 4,941,881 to Masters et al and in U.S. Pat. No. 5,498,241 to Fabrozzi. Not only can blood-splash occur through the open front ends of these guards, but the wide slot provides another route for blood-splash and may also allow the guard and needle to be misaligned so that the point of a guarded needle can extend through the slot.

The third type of guard of the first class is that suited for use with wingless needles. A guard of this type take the form of a tapered sleeve into which the hub of a used needle can be pulled by its tube and jammed in the rear end thereof(eg, U.S. Pat. No. 5,401,250 to Shields). However, blood-splash can still occur from the open front end of the sleeve and frictional jamming is an insecure manner of securing the needle and its hub in a guard.

The second class of guard (where the needle is permanently mounted in the guard) is well represented in the art; for example, U.S. Pat. No. 4,676,783 to Jagger et al, U.S. Pat. No. 5,088,982 to Ryan, U.S. Pat. Nos. 5,112,311, 5,290,264 & 5,433,703 to Utterberg, and U.S. Pat. No. 5,120,320 to Fayngold. Not only do such guards generally have open front ends through which blood-splash can occur, but the slots formed to slidingly accommodate the needle wings provide additional apertures through which blood-splash may occur and can allow the point of the needle itself to protrude. In one case (Utterberg U.S. Pat. No. 5,112,311 FIGS. 23–25), the slots are fitted with 'curtains' or flaps (identified by numeral 403 by Utterberg) to mitigate this danger but, if the curtains are to be effective in that regard, they will make it difficult to move the wings of the needle assembly along the slots. In another case (U.S. Pat. No. 5,433,703 to Utterberg), a separate cap is provided for covering the open end of the guard after the needle has been withdrawn therein, but the cap is another item to manipulate and is an additional expense. Not all guards of the second class are for use with winged needles. For example, U.S. Pat. No. 5,382,240 to Lam and European patent 722,749 to BOC Group disclose needle guards within which wingless needle assemblies are slidingly mounted. The first of these has an open front end while, in the second, the needle hub is provided with stubby wing-like protrusions that ride in side slots formed a tubular housing. Though both such end and side openings provide the opportunity for blood-splash contamination, the BOC patent is of particular interest because it discloses the use of a sliding or hinged gate on the front end of the guard that can be manually operated to close that end after the needle has been withdrawn into the guard tube. Again, however, the addition of such gates is expensive and possibly unreliable since they require additional and separate moving parts.

OBJECTIVES OF THE INVENTION

It is therefore an object of the present invention to provide guards for use with medical needle assemblies, and to provide combined guards and needle assemblies, which will address at least some of the practical disadvantages of the guards and combinations of the prior art while minimising the danger of needle-stick injury and blood-splash contamination.

OUTLINE OF INVENTION

The present invention is based upon the realisation that the normally-open front end of a guard with a tubular body can be manually or automatically closed over a needle that has been withdrawn therein by bringing together the front extremities of two opposed sidewalls of the body to close the front opening. This can be effected by utilising the resilience of one or both of the sidewalls, by fitting—and, if desired, clipping—one sidewall into the other under finger pressure, by inverting the front end of one sidewall into the other or by arranging for one or both sidewalls to pivot and close the front aperture as the hub of the needle assembly is pulled home. Such safety features are applicable to needle guards in all the classes and types reviewed above, whether they be for use with wingless or winged needle assemblies. Unlike the Nicoletti guard, there can be no contact between the user and the needle while the front end of the guard is being closed and, unlike Utterberg (in U.S. Pat. No. 5,433,703) and BOC, no additional caps or gates are required to effect such closure.

Where the guard is to be used with a winged needle assembly, the front portions of the two sidewalls may be separate so that they can move apart to allow the wings of the needle hub to slide rearwardly therebetween into a rear portion or chamber of the guard where the wings are captured in side holes (as in our prior US patent referred to above). The sidewall which is normally upper-most in use is preferably stiff and of a concave section that is, preferably, deeper than the thickness of the trailing tube of the associated needle assembly. On the other hand, the opposing—normally lower—sidewall is preferably flexible, tongue-like and shaped to fit within the upper sidewall, where it may be locked under finger pressure by click-action. These sidewalls can also usefully combine to form the side holes of the rear chamber of the guard in which the hub and its wings are captured. At least portion of the front edges of the side holes can be formed by upstanding ramp-like side elements on the rear of one of the sidewalls (preferably the lower one) so as to ensure that the wings of a needle assembly are normally blocked from moving forwards once they have entered the side holes.

The upper sidewall of the above type of split guard can be provided with an outwardly and horizontally-extending peripheral flange around the bottom edge of its front end so that (i) a broader surface area is provided for resting on the arm of the donor or patient, (ii) the finger and thumb of a user are prevented from extending below the bottom edge when the upper sidewall is gripped between thumb and finger at its front end while the needle is being withdrawn from the donor or patient and simultaneously pulled into the guard. To improve the grip of the front portion of the upper sidewall, it may have a generally rectangular section and provided with shallow external ribs. In addition, the rear end of the upper part of the guard may recessed to provide a pad for the thumb of the user.

In an alternative form of guard, both top and bottom sidewalls may be of concave shape to form a tube-like body. In that case, the front extremities of the sidewalls can be formed so that, when pressed between the fingers, one collapses or inverts into the other to close off the front end of the guard, thus securing the used needle inside. This type of closure may be used with open slit or open-slotted guards for use with standard pre-formed needle assemblies, with guards having closed slots that have captive winged needles, and, with un-split and un-slotted guards for use with wingless needle assemblies. Inwardly and rearwardly extending barbs may be included within such guards to lock the needle hubs in the rear thereof before their ends are closed.

The guards of the invention can be injection-moulded as a pair of hinged sub-members that can be folded and clipped, glued or welded together around the tube of a preformed needle assembly. Alternatively, the guards can be moulded as two separate halves that are assembled around the tube by clipping, gluing or welding. Adsorbent pads may be attached to the inside surface of the guard in the vicinity of the point of a needle located in the guard so as to immobilise drops of blood or other liquid exuded from the needle. This objective may also be achieved by roughening the internal surfaces of one or both sidewalls.

It should be noted that, while the invention is primarily concerned with needle guards per se, it is also concerned with the combination of a captured winged needle assembly and guard where the guard is of the type having closed-end wing-slots. It should also be noted that the terms 'upper', 'lower', 'vertical' and horizontal' are used as a descriptive convenience. They are not intended literally, nor do they suggest that a guard must be maintained, held or used in any particular orientation.

DESCRIPTION OF EXAMPLES

Having broadly portrayed the nature of the present invention, particular examples will now be described by way of illustration only. In the following description, reference will be made to the accompanying drawings in which:

FIG. 1 is a perspective view of the assembled needle guard that forms the first example;

FIG. 2 is a perspective view of the interior of the guard of FIG. 1 in the unfolded or un-assembled state;

FIG. 3 is a perspective view of the exterior of the guard of FIG. 1 in the unfolded or un-assembled state;

FIGS. 4a, 4b and 4c are sectional diagrammatic elevations of the guard of the first example showing a winged needle assembly just after insertion of the needle (FIG. 4a), as it is being withdrawn into the guard (FIG. 4b) and after it has been fully withdrawn into the guard (FIG. 4c);

FIG. 5 is a cross-section of the guard of FIG. 1 taken on section plane 5—5 indicated in FIG. 1;

FIG. 6a is a longitudinal sectional elevation of the guard which forms the second example of the invention with its front end open, and FIG. 6b is an enlarged view of the front end of the guard of FIG. 6a taken on plane 6—6 shown in FIG. 6a;

FIG. 7a is a longitudinal sectional elevation of the guard of FIG. 6a with its front end closed, and FIG. 7b is an enlarged view of the front end of the guard of FIG. 7a taken on plane 7—7 of FIG. 7a;

FIG. 8a is a longitudinal sectional elevation of the guard which forms the third example of the invention with its front end open, FIG. 8b is an enlarged view of the front end of the guard of FIG. 8a with its front end open, while FIG. 8c is an enlarged end view of the same guard with its front end closed, FIGS. 8b and 8c being viewed as indicated by plane 8—8 in FIG. 8a;

FIG. 9 is a longitudinal sectional elevation of the guard which forms the fourth example of the invention with a wingless needle captured therein;

FIG. 10a is a longitudinal sectional elevation of the guard which forms the fifth example of the invention showing the needle and needle hub partially withdrawn into the guard, while FIG. 10b is a similar view of the same guard showing the needle and its hub fully withdrawn into and shielded by the guard.

Referring now to FIGS. 1 to 3, the first example is a guard 10 of the first class and first type indicated above; that is, it is intended for attachment to the trailing tube of a preformed standard winged-needle assembly. Guard 10 has a body that can be functionally divided into a rear chamber portion 12 adapted to accommodate the winged hub 14 of a needle assembly 16 (see FIGS. 4a–4c) and a front sidewall portion 18 that guides the winged hub 14 rearwardly into chamber 12. The upper face of the rear portion of chamber 12 is recessed or depressed at the rear to form a thumb-pad 17, the use of which will be explained below. Since guard 10 is for use with winged needle assemblies, chamber 12 has opposing side holes 20 to accommodate the wings 22 of a winged hub 14 located in chamber 12. Guard 10 is conveniently injection-moulded from a resilient plastics material such as PVC or polypropylene as a pair of complementary shell-like sub-members 24 and 26 joined by an integral strip-form hinge 28. For convenience, sub-members 24 and 26 will be referred to as the upper and lower sub5 members, respectively.

Upper sub-member 24 has a rear portion 24a joined to a front sidewall 24b that terminates forward at a front end or extremity 30. Similarly, lower sub-member 26 has a rear portion 26a and a front sidewall 26b that terminates at a front end or extremity 31. When sub-members 24 and 26 are folded together rear portions 24a and 26a form chamber 12a and sidewalls 24b and 26b form sidewall portion 18 of guard 10. Two hooked pegs 32 are integrally moulded on rear portion 24a of upper sub-member 24 and a complementary pair of sockets 34 are formed in the rear portion 26a of lower sub-member 26 so that, after folding, sub-members 24 and 26 can be permanently secured together about the trailing tube 36 of a winged needle assembly 16 (see FIGS. 4a to 4c) by entering pegs 32 into sockets 34. In this way, guard 10 is formed around tube 36 for sliding movement thereon. Sub-members 24 and 26 have rear walls 38 and 40 which have central recesses 42 and 44 that come together to form the rear aperture 46 (see FIGS. 4a–4c) in guard 10 through which tube 36 passes, while front ends 30 and 31 of sidewalls 24b and 26b come together to form a closable front aperture of the guard.

Upper sidewall 24b is of generally rectilinear form and has concave inner surface throughout its length so that it is stiff and of an inverted-U shape. Preferably, the depth of upper sidewall is greater than the diameter of trailing tube 36 so that lower sidewall 26b is always located and guided by upper sidewall 24b. The lower peripheral edge of upper sidewall 24b is flared outwards to form a flange 48 to (i) assist guard 10 ride over wings 22, (ii) provide a firm and comfortable base for the guard on which to rest against the skin of the patient or donor, (iii) provide an additional area for gripping by the user and (iv) to inhibit the user's finger and thumb from extending below upper sidewall 24b. Preferably, the exterior of upper sidewall 24b is provided with a series of ribs 50 to form a non-slip finger-grip.

The lower sidewall 26b has ramp-like up-standing vertical side elements 52 toward the rear that terminate in rear10 facing abutments 53. Ramp elements 52 stiffen sidewall 26b while abutments 53 form portion of the front periphery of holes 20 that prevents the wings 22 of a needle assembly 16 moving forwards out of chamber 12. Lower sidewall 26b is narrow enough throughout its length for it to fit within the inverted-U of upper sidewall 24b, as is shown by the sectional drawing of FIG. 5. Thus, upper sidewall 24b serves to laterally and vertically guide the more flexible lower sidewall 26b, keeping it aligned with upper sidewall 24b at all times.

The front portion of lower sidewall 26b is tapered to form an upwardly curved flat tongue 54 that terminates in the downwardly sloping end or tip 31, the curve of tip 31 assisting tongue 54 ride over the butt end of hub 14 when it is drawn rearwards into the guard 10. Sidewall 26b and its tongue 54 are arranged to resiliently bias end 31 against the inner surface of end 30 of upper sidewall 24b so that (in the absence of trailing tube 36) the front aperture of guard 10 is normally closed, preventing blood-splash from that quarter. Also, since lower sidewall 26b always lies between the sides of upper sidewall 24b, there is no side slot or gap between upper and lower sidewalls 24b and 26b through which blood-splash may occur or through which the point of the needle 56 (FIGS. 4a–4c) of assembly 16 may protrude, yet a winged needle hub 14 can be pulled into guard 10 by its tube 36 by temporarily deflecting lower sidewall 26b away from upper sidewall 24b.

The use of guard 10 will now be described with respect to FIGS. 4a to 4c, assuming that guard 10 has been clipped together around trailing tube 36 of needle assembly 16 as previously described. Though guard 10 can be easily slipped along tube 36, it is lightly and resiliently gripped between tongue 54 and the underside of upper sidewall 24b so that the guard cannot slip along the tube under gravity to either interfere with the use of the needle 56 or make the guard inconvenient to grasp when it is needed. As will be seen from FIG. 4a, needle 56, hub 14 and wings 22 can all be used in an entirely conventional manner without interference from the guard 10 to tap the vein 58 in the arm 60 of a donor or patient.

When needle 56 is to be withdrawn from arm 60, guard 10 is slipped forwards along tube 36 and onto hub 14 with sidewall 24b uppermost. In so doing, lower sidewall 26b is deflected downwards to accommodate hub 14 and its wings 22. A swab 62 is placed on the puncture site and pressed down by the thumb 64 of the user's left hand while a finger 66 of that hand is used to hold the front end of guard 10 against arm 60. Tube 36 is gripped in the palm of the right hand 68 while the thumb 70 of that hand is placed on thumb-pad 17, as shown in FIG. 4b. By straightening right thumb 70, tube 36 pulls needle 56 from arm 60 directly into the front end of guard 10, entry of hub 14 and wings 22 of assembly 16 into guard 10 being facilitated by the flexibility of tongue 54 of lower sidewall 26b and the curved tip 31.

While the technique just described is satisfactory and convenient to illustrate, a different method is preferred. In this method, the front portion of upper sidewall 24b is gripped between the thumb and the second finger of the left hand and the swab 62 is pressed down with the third finger of that hand, the use of the right hand being as shown and described above. This allows guard 10 to be lifted from arm 60 so that a more comfortable angle of needle withdrawal can be assumed and so that tongue 54 can flex downwards without pressing on arm 60, facilitating entry of hub 14 and wings 22 into guard 10 along and between sidewalls 24b and 26b.

As hub 14 and wings 22 enter guard 10, end 31 of sidewall 26b rides over them and moves down allowing them to pass rearwards. Upon further withdrawal, wings 22 contact ramp-like edges 52 forcing sub-member 26b further away from upper sub-member 24b until hub 14 enters chamber 12 and wings 22 drop into side holes 20. Lower sub-member 26b therefore returns to its normal position in which it is entirely contained within upper sidewall 24b, closing any side gaps between the sidewalls, and in which end 31 of tongue 54 closes off the front aperture of the guard by returning to rest on the underneath of the front end 30 of upper sidewall 24b. It will be noted that, while needle 56 and hub 14 are being withdrawn to the shielded position in the guard as shown in FIG. 4c, sidewalls 24b and 26b act to shield a user's fingers from contact with the sides of the needle 56. Finally, to lock lower sidewall 26b within upper sidewall 24b, the user presses the sidewalls together, forcing lower sidewall 26b further into sidewall 24b to move it passed protuberances or catches 72 (see FIGS. 2 and 5) on the inside side faces of upper sidewall 24b.

It will be appreciated that guard 10 of the first example provides a simple, convenient and highly cost-effective means of protecting medical workers from needle-stick and blood-splash. Moreover, it will be appreciated that guard 10 can be used just as effectively with wingless needles as with winged needles, though side holes 20 of chamber 12 would then be omitted. In that event, internal flexible and rearwardly facing barbs could be formed near the rear of either or both sidewalls 24b and 26b to engage and retain the hub of the wingless needle assembly.

It will also be appreciated that, instead of or in addition to catches 72, the inverted-U of the upper sidewall 24b may be given a re-entrant shape near or at its end 30. The end 31 of tongue 54 may then formed with a convex section so that it will be self-guided into the upper sidewall and, by flexing laterally, snap into and be retained by the upper sidewall.

It will be noted that, since lower sidewall 26b is a little shorter than upper sidewall 24b, tip 31 of tongue 54, is covered by the front end 30 of upper sidewall 24b so that it is not readily accessible (FIG. 1). This prevents tongue 54 or tip 31 catching on something and pulling lower sidewall 26b away from upper sidewall 24b to expose guarded needle therein.

Referring now to FIGS. 6a to 7b, the guard 80 of the second example has a body 82 in the form of a simple one-piece moulded-plastic tube fitted to slide axially on the trailing tube 84 of a wingless needle assembly 86 at the time of manufacture of the assembly. Body 82 has an open front end 88 and a rear end 90 that is closed except for a rear aperture 92 of a diameter sufficient to slidingly accommodate trailing tube 84. Rear aperture 92 is not large enough to allow the hub 94 of assembly 86 to pass therethrough. Front end 88 of body 82 is preferably of a larger diameter than rear end so that (i) entry of hub 94 is facilitated and (ii) hub 94 fits snugly in the rear portion 95 of body 82 which serves as the chamber 12 of FIG. 1.

In this example, body 82 is moulded so that it has an upper sidewall 96 and a lower sidewall 98 separated by longitudinal external grooves or creases 100. Though not shown in FIGS. 6a and 6b, upper sidewall 96 is preferably thicker—especially at its forward extremity 102—than lower sidewall 98 at its forward extremity 104. The different thicknesses of the sidewalls ensures that upper sidewall 96 is stiffer than lower sidewall 98 so that forward extremity 104 of lower sidewall 98 can be inverted into forward extremity 102 of upper sidewall 96 (as shown in FIGS. 7a and 7b) by simply pressing the front end of the body 82 between the fingers so as to collapse it. Again, it will be noted that, as needle assembly 86 is withdrawn into guard 80, contact by the user's fingers with that portion of assembly 86 to the rear of guard front end 88 is prevented.

It will be appreciated that, besides simplicity of design, guard 80 of the second example has the advantage that it can serve as a shielded package for an unused wingless needle assembly as well as a safety guard for the same needle after use. It will also be appreciated that simple tubular guards of this type can be moulded as a pair of hinged semi-cylindrical sub-members which can be folded and snapped together. Such a configuration makes it convenient to mould rearward facing barbs or prongs 106 into each sub-member for the purpose of capturing needle hub 74 in rear chamber 95 of the guard as an added safety measure. Such a configuration also allows a guard 80 to be assembled by the user around the trailing tube 84 of a standard pre-manufactured needle assembly. Barbs 106 preferably make light frictional contact with trailing tube 84 so that the guard 80 will not slip along the tube under gravity.

The third example relates to a guard 120, illustrated in FIGS. 8a–8c, that is a modification of guard 80 of the second example to allow accommodation of a winged needle assembly 121. As before, guard 120 has a tubular body 122 with an open front end 124 and closed rear end 126 provided with a rear aperture 128 for the trailing tube 130 of a needle assembly 121. Body 122 is also divided into an upper sidewall 134 and a lower sidewall 136 and, again, the region of upper sidewall 134 near its front extremity 138 is preferably thicker and stiffer than the region near the front extremity 140 of lower sidewall 136. In this example, however, the sidewalls are separated by a pair of longitudinal slots 142 that take the wings 144 on the hub 146 of needle assembly 121.

Wing slots 142 may extend into the front aperture 124 of body 122, as illustrated in FIGS. 8a–8c, or they may stop a little short of the front extremities 138 and 140 of the sidewalls 134 and 136, leaving these extremities joined by a short strip 148 indicated by dotted lines. In the former case, body 122 could be moulded as a unitary tube since the winged needle hub can be pulled rearwards into the open wing slots 142. This allows the needle to be used in the normal manner without interference by the guard 120. In the latter case, body 122 needs to be moulded as two separate parts that can be assembled around winged needle assembly 121, or as two connected sub-members that can be hinged together and fitted onto the assembly. This allows inwardly and rearwardly projecting barbs 150 to be moulded into body 122. Again, if closed wing slots are employed, it may be convenient to fit the guard onto the needle assembly during manufacture of the assembly.

To use guard 120 with a captured needle assembly 121, hub 146 and wings 148 are pushed forward to the front end of slots 142 so that the needle 152 protrudes from the front aperture 124. Needle 152 is then inserted as require, albeit with some interference from the guard 120. At the completion of the procedure, the needle is withdrawn from the patient directly into guard 120, wings 144 being pulled back to the rear end of the slots 142. Whereupon, front end 140 of sidewall 136 is collapsed (ie, inverted) into front end 138 of sidewall 134, trapping the needle 152 in place within the guard in such a manner that blood-splash from the front end of the body 122 of guard 120 or from slots 142 cannot occur. Finally, to lock lower sidewall 136 into upper sidewall 134 when sidewall 136 is inverted, the upper edges of slots 142 may be enlarged inwards as shown at 154 in FIGS. 8b and 8c.

The fourth example of a guard 200 formed in accordance with this invention is illustrated in longitudinal section in FIG. 9. Again, this guard has a simple tube-like body 202 with upper and lower sidewalls 204 and 206 which are best moulded as upper and lower sub-members that are joined together in the rear chamber portion 208 but are otherwise separable along central split line 210. Again, the rear end 212 of body 202 is closed except for rear aperture 214 through which trailing tube 216 of needle assembly 218 can pass, the needle assembly including hub 220 and needle 222.

In this example, however, guard 200 is preferably of rectangular section and front aperture 224 of body 202 is only formed by trailing tube 216 of needle assembly 218 passing therethrough. In the absence of the tube 216, aperture 224 is closed by inwardly and rearwardly sloping lips 226 and 228 (formed integrally with upper and lower sidewalls 204 and 206, respectively) which are biased together. As in the previous examples, inwardly and rearwardly facing barbs 230 may be employed to retain hub 220 in rear portion or chamber 208, if desired.

Guard 200 is capable of accommodating winged or wingless needle assemblies, a wingless needle assembly 218 being illustrated. The only difference in the case of a winged assembly need be the incorporation of side holes in chamber 208 (like those indicated at 20 in the first example and shown in FIG. 1), slits 210 opening into such side holes to guide the needle wings thereto. The provision of side holes to capture the wings of a winged needle assembly obviates the need for the use of barbs 230.

In use, guard 200 is fitted to trailing tube 216 of wingless needle assembly 218 behind and clear of hub 220, and needle 222 is inserted in the normal manner. When it is time to remove needle 222, guard 200 is moved forwards along trailing tube 216 until it contacts the rear end of hub 220, whereupon a swab is applied to the wound. Tube 216 is then pulled to draw hub 220 and needle 222 into body 202. The pressure by hub 220 on sloping lips 226 and 228 causes the sidewalls 204 and 206 to move further apart against their inherent bias and, therefore, to open front aperture 224 sufficiently to allow the hub 220 to enter the body 202 of guard 200 (in addition to tube 216). The tube is pulled rearwards until hub 220 and needle 222 are fully enclosed in the guard, allowing and upper and lower sidewalls 204 and 206 to spring back and cause lips 226 and 228 to close front aperture 224. Preferably, hub 220 is pulled right into rear chamber 208 behind barbs 230 (if present). Again the user's fingers are shielded from contact with any part of hub 220 and needle 222 withdrawn to the rear of front aperture 224.

As an optional feature, clips (not shown) may be provided on the mating edges of upper and lower sidewalls 204 and 206 and/or on the mating edges of lips 226 and 228. This allows the sidewalls 204 and 206 of body 202 to be locked or clipped together in a positive manner by simply pressing the sidewalls 204 and 206 together between the fingers after the needle has been safely stowed.

The fifth and final example of the invention is guard 250 illustrated in FIGS. 10a and 10b which, again, may have a body 252 of rectangular section. In this case however, upper and lower sidewalls 254 and 256 (respectively) are formed as separate pivoting levers mounted in body 252 to pivot about horizontally and transversely disposed shafts 258 and 260 (respectively). The portion of body 252 between shafts 258 and 260 forms a rear chamber 262 into which the hub 264 of a needle assembly 266 can be withdrawn by pulling on its trailing tube 268. FIG. 10a shows needle hub 264 just prior to entering chamber 262 and FIG. 10b shows hub 264 fully withdrawn into chamber 262. If desired, rearwardly and inwardly facing flexible barbs 270 and 272 can be formed on the inner faces of sidewalls 254 and 256 near shafts 258 and 260(respectively). It will be noted that the portions of the pivoting sidewalls 254 and 256 to the rear of shafts 258 and 260 are formed at an obtuse angle to the portions of the respective sidewalls forward of shafts 258 and 260.

In this example, the front ends or forward extremities 254a and 256a of sidewalls 254 and 256 define between them (together with other walls 273 of body 252) the front aperture 274 of the guard 250 and body 252. Sidewall ends 254a and 256a are out-turned to facilitate the rearward entry of needle hub 264 therebetween.

Preparatory to use, guard 250 is fitted to and positioned on trailing tube 268 of assembly 266 in a similar manner to that described for previous examples, leaving the needle hub 264 and needle 276 well clear of the guard 200. After use, the needle 276 is drawn out of the arm of the patient or donor straight into the front aperture 274 between the front extremities 254a and 256a of sidewalls 254 and 256, forcing them a little further apart. In FIG. 10a, needle hub 264 and needle 276 are shown partially withdrawn into guard 250 and it will be seen that the user's fingers cannot contact that portion of the needle to the rear of front end of guard 250. Upon further withdrawal by pulling on tube 268, the rear of hub 264 contacts barbs 270 and 272 (if present) swinging front ends 254a and 256a of sidewalls 254 and 256 together, closing front aperture 274. Further withdrawal sees hub 264 contact the rear ends of sidewalls 254 and 256, holding their front extremities 254a and 256a together while releasing barbs 270 and 272 to trap hub 264 in rear chamber 262 of body 252. Preferably, the front portions of sidewalls 254 and 256 are flexible and resilient, bending under the force of contact to firmly close the front aperture 274 between them and safely secure needle 276 in the guard.

While it will be appreciated that the five examples of the invention described meet the objectives of the invention and address many of the problems in the art, many modifications and alterations may be made thereto without departing from the scope of the invention as defined in the following claims.

What is claimed is:

1. A needle guard for use with a medical needle assembly in which a needle extends forwardly and axially from a hub to a point and a flexible tube extends rearwardly and axially from the hub, wherein:

the guard has an axially extending elongate tubular body having a front end and a rear end, said body being adapted to accommodate the hub and needle of the needle assembly in a shielded position therein, said front end of the body has a front aperture through which the needle and hub of the needle assembly can be axially and rearwardly withdrawn to bring the hub and needle into the shielded position within the body, a chamber is provided within the rear end of the body to accommodate the hub of the needle assembly when the hub and the needle are in the shielded position within the body, a rear aperture is formed in the chamber through which the tube of the needle assembly can extend so that the hub of the needle assembly can be withdrawn into the chamber from the front end of the body by the tube of the needle assembly, a first sidewall of the body extends forwardly from said chamber to said front aperture, said first sidewall having a front end that at least partially defines the front aperture, a second sidewall of the body extends forwardly in opposed spaced relation to said first side wall from said chamber to said front aperture, and second sidewall also having a front end that at least partially defines said front aperture, said front end of the first sidewall and said front end of the second sidewall are adapted to be brought together and retained together to close the front aperture so as to enclosed a needle and hub in the shielded position within the body, and the first sidewall and the second sidewall cooperate to shield the portion of the needle to the rear of the front aperture from possible side contact with a user's fingers during withdrawal of the hub and needle into the shielded position within the body of the guard.

2. A needle guard according to claim 1 wherein:

at least one of the first and second sidewalls is sufficiently flexible and resilient to (i) cause the tube of a needle assembly which passes through the front aperture to be resiliently gripped between the front ends of the sidewalls and (ii) to close the front aperture after the needle assembly has been withdrawn into to the guard.

3. A needle guard according to claim 1 wherein:

the first and second sidewalls are separable from one another to enable the front ends thereof to be moved apart and together to thereby effect the opening and closing, respectively, of said front aperture, the first sidewall has a concave section having a greater depth and stiffness relative to the second sidewall, the second sidewall is thin and flexible relative to the first sidewall and is adapted to fit within said concave section of the first sidewall and to resiliently bias the second extremity toward the first extremity to tend to close the front aperture, the tube, hub and needle of a needle assembly are substantially contained within the depth of the section of the first sidewall as they are drawn into the body through said front aperture, and the needle of a needle assembly is contained within the depth of the section of the first sidewall and between said first and second sidewalls during and after withdrawal into the guard.

4. A guard according to claim 3 wherein:

the concave section of the first sidewall has opposing internal surfaces that are generally parallel and axially extending, catch means are provided on said opposing internal surfaces adapted for engagement with the second sidewall so that, under finger pressure, the second sidewall can be engaged with said catch means by a snap-action to positively retain the second sidewall between said opposing internal surfaces of the first sidewall, whereby the front ends of the sidewalls are brought into resilient contact to thereby close the front aperture so that a needle contained within the guard is entirely enclosed by the coaction of said sidewalls.

5. A guard according to claim 3 for use with a winged needle assembly wherein the hub of the assembly is provided with lateral wing-like extensions, wherein:

said chamber has two opposing side holes shaped to accommodate corresponding wings of the winged needle assembly so that, when the hub of the assembly is withdrawn into the chamber, the wings will be accommodated by said holes to extend laterally therefrom, and wherein at least one forwardly facing ramp element is provided on the second sidewall extending toward the first sidewall and having a rear abutment substantially coinciding with the front periphery of said holes, so that a wing of the needle assembly can drawn reawardly along said ramp element until it enters one of said side holes, whereupon its forward movement will be inhibited by said rear abutment.

6. A guard according to claim 5 wherein:

the body of the guard is formed by a first elongate and axially extending sub-member and a second elongate and axially extending sub-member, the first sub-member includes the first sidewall and a first portion of said chamber to rear of said side holes, the second sub-member includes the second sidewall and a second portion of said chamber to the rear of said side holes, hinge means joining said first and second portions of said chamber so that the first and second sub-members can be hinged together about the tube of a needle assembly to thereby form said chamber and said side holes, and locking means located opposite said hinge means in said chamber adapted to lock the sub-members together after they have been hinged together to form said body.

7. A needle guard according to claim 1 wherein:

the first and second sidewalls each have a concave internal section and are joined together along substantially their entire lengths to form said tubular body, the front end of the second sidewall is adapted to invert to adopt a convex internal form, under finger-pressure by a user, and to be stably retained within and by the front end of the first sidewall in an inverted condition after said finger-pressure has been released, to thereby close the front aperture after the needle and hub have been withdrawn to the shielded position.

8. A needle guard according to claim 1 wherein:

the first and second sidewalls each have a concave internal form and are joined together near the front ends thereof, a pair of opposed axially-extending slots are formed between the first and second sidewalls intermediate of said joined rear portion and front ends, said slots being adapted to slidingly accommodate the wings of a winged needle assembly so as to capture the hub of the assembly within the body of the guard for movement between a forward position in which the needle extends from said front aperture and a shielded position in which the needle is entirely housed within the body of the guard, the front end of the second sidewall is adapted to invert to adopt a convex internal section, under finger-pressure by a user, and to be stably retained within and by the front end of the first sidewall in an inverted condition after said finger-pressure has been released, to thereby close the front aperture after the needle and hub of the needle assembly have been withdrawn to the shielded position within the body of the guard.

9. A needle guard according to claim 1 wherein:

the front end of at least one of the sidewalls is formed with in inwardly and reawardly sloping lip that, together with the front extremity of the other side wall, defines the front aperture, so that the so that the front ends of the sidewalls will be moved apart by abutment of the hub against said lip as the hub of the needle assembly is withdrawn into the shielded position in the body of the guard.

10. A needle guard according to claim 1 wherein:

the first sidewall is pivotally mounted within the body about a transverse pivot axis located intermediate of the front and rear ends of the body, the first sidewall having a rear part that its located to the rear of said pivot axis and a front part that is located to the front of the pivot axis, the arrangement of the first sidewall is such that, when the needle assembly is pulled rearwards through the front aperture, contact between the hub and the front end of the first sidewall will cause said front part to pivot away from the second sidewall so as to permit the needle hub to enter the body of the guard, and wherein the arrangement of the first sidewall is such that, when the hub of a needle assembly is drawn into the body of the guard to the rear of the pivot axis, the hub will contact the rear part of the first sidewall and cause said rear part to pivot outwards thereby causing the front end of the first sidewall to pivot inwards to effect the closure of the front aperture to thereby enclose the needle of the needle assembly within the body of the guard.

11. A needle guard according to claim 1 wherein:

the first sidewall is pivotally mounted within the body about a first transverse pivot axis located intermediate of the front and rear ends of the body, the first sidewall having a rear part that its located to the rear of said pivot axis and a front part that is located to the front of the pivot axis, the second sidewall is pivotally mounted within the body about a second transverse pivot axis located intermediate of the front and rear ends of the body, the second sidewall having a rear part that its located to the rear of said second pivot axis and a front part that is located to the front of the second pivot axis, the arrangement of the first and second sidewalls is such that, when the needle assembly is pulled rearwards through the front aperture, contact between the hub and the front ends of the first and second sidewalls will cause the respective front parts of the first and second sidewalls to pivot away from one another permit the needle hub to enter the body of the guard, and wherein the arrangement of the sidewalls is such that, when the hub of a needle assembly is drawn into the body of the guard to the rear of said pivot axes, it will contact said rear parts of the sidewalls and cause them to pivot outwards thereby causing said front parts of the sidewalls to pivot inwards and to effect the closure of the front aperture to thereby enclose the needle and hub of the needle assembly in the shielded position within the body of the guard.

12. A needle guard according to claim 7 wherein:

at least one rearward facing barb extends inwards from at least one of the sidewalls just forward of the chamber so that, as the hub of a needle assembly is withdrawn into the chamber, the barb is resiliently deflected to allow the hub to pass and so that, after the hub has passed, the barb will spring back to prevent the hub from moving forwards in the body of the guard.

\* \* \* \* \*